(12) United States Patent
Lecuivre et al.

(10) Patent No.: US 10,342,652 B2
(45) Date of Patent: Jul. 9, 2019

(54) BARBED PROSTHETIC KNIT AND HERNIA REPAIR MESH MADE THEREFROM AS WELL AS PROCESS FOR MAKING SAID PROSTHETIC KNIT

(71) Applicant: Sofradim Production, Trévoux (FR)

(72) Inventors: Julie Lecuivre, Jassans-Riottier (FR); Xavier Bourges, Saint Etienne sur Chalaronne (FR); Pierre Bailly, Caluire-et-Cuire (FR)

(73) Assignee: Sofradim Production, Trévoux (FR)

( * ) Notice: Subject to any disclaimer, the term of this patent is extended or adjusted under 35 U.S.C. 154(b) by 232 days.

(21) Appl. No.: 15/262,165

(22) Filed: Sep. 12, 2016

(65) Prior Publication Data

US 2016/0374792 A1 Dec. 29, 2016

Related U.S. Application Data

(63) Continuation of application No. 14/366,393, filed as application No. PCT/EP2012/076981 on Dec. 27, 2012, now Pat. No. 9,445,883.

(30) Foreign Application Priority Data

Dec. 29, 2011 (FR) ...................... 11 62535

(51) Int. Cl.
*A61F 2/02* (2006.01)
*D04B 21/12* (2006.01)
(Continued)

(52) U.S. Cl.
CPC ............ *A61F 2/0063* (2013.01); *D04B 21/12* (2013.01); *D04B 21/14* (2013.01); *D04B 21/20* (2013.01);
(Continued)

(58) Field of Classification Search
CPC . A61F 2/0063; A61F 2002/0068; D06C 7/00; D04B 21/20; D04B 21/12;
(Continued)

(56) References Cited

U.S. PATENT DOCUMENTS

| 1,187,158 A | 6/1916 | Mcginley |
| 3,118,294 A | 1/1964 | Van Laethem |

(Continued)

FOREIGN PATENT DOCUMENTS

| CA | 1317836 C | 5/1993 |
| DE | 19544162 C1 | 4/1997 |

(Continued)

OTHER PUBLICATIONS

Australian Patent Examination Report dated Aug. 15, 2016 in corresponding Australian Patent Application No. 2012360855, 2 pages.

(Continued)

*Primary Examiner* — Julian W Woo

(57) ABSTRACT

The present invention relates to a prosthetic knit based on at least a first yarn of biocompatible polymer material defining first and second opposite and openwork faces, and on at least a second biocompatible and heat-fusible monofilament yarn, forming barbs that protrude outwards from at least said first face and are obtained by melting loops generated by said second yarn, the chart followed for the knitting of said first and second yarns on a warp knitting machine having three guide bars B1, B2, B3 being the following, according to the ISO 11676 standard:—Bar B1: 1.0/0.1//—Bar B2: 1.0/7.7/ 6.6/7.7//—Bar B3: 2.1/5.5/3.4/0.0// said second yarn following the chart of bar B3. The present invention also relates to a process for manufacturing such a knit.

20 Claims, 2 Drawing Sheets

(51) Int. Cl.
*D04B 21/14* (2006.01)
*D04B 21/20* (2006.01)
*D06C 7/00* (2006.01)
*A61F 2/00* (2006.01)

(52) U.S. Cl.
CPC ........ *D06C 7/00* (2013.01); *A61F 2002/0068* (2013.01); *A61F 2220/0016* (2013.01); *A61F 2240/001* (2013.01); *D10B 2401/041* (2013.01); *D10B 2403/0111* (2013.01); *D10B 2501/0632* (2013.01); *D10B 2509/08* (2013.01)

(58) Field of Classification Search
CPC ........ D10B 2403/0111; D10B 2401/12; D10B 2509/08; D10B 2501/0632
See application file for complete search history.

(56) References Cited

U.S. PATENT DOCUMENTS

| | | |
|---|---|---|
| 3,124,136 A | 3/1964 | Usher |
| 3,272,204 A | 9/1966 | Charles et al. |
| 3,276,448 A | 10/1966 | Usher |
| 3,320,649 A | 5/1967 | Naimer |
| 3,364,200 A | 1/1968 | Ashton et al. |
| 3,570,482 A | 3/1971 | Emoto et al. |
| 4,006,747 A | 2/1977 | Kronenthal et al. |
| 4,060,081 A | 11/1977 | Yannas et al. |
| 4,173,131 A | 11/1979 | Pendergrass et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,846,815 A * | 7/1989 | Scripps .............. A44B 18/0019 604/391 |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 5,002,551 A | 3/1991 | Linsky et al. |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | McMurray |
| 5,350,583 A | 9/1994 | Yoshizato et al. |
| 5,356,432 A | 10/1994 | Rutkow et al. |
| 5,368,549 A | 11/1994 | McVicker |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,681,568 A | 10/1997 | Goldin et al. |
| 5,686,115 A | 11/1997 | Vournakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,709,934 A | 1/1998 | Bell et al. |
| 5,716,409 A | 2/1998 | Debbas |
| 5,720,981 A | 2/1998 | Eisinger |
| 5,732,572 A | 3/1998 | Litton |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | McGregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |

(56) References Cited

U.S. PATENT DOCUMENTS

| | | |
|---|---|---|
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Kovac |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,120,539 A | 9/2000 | Eldridge et al. |
| 6,132,765 A | 10/2000 | DiCosmo et al. |
| 6,143,037 A | 11/2000 | Goldstein et al. |
| 6,153,292 A | 11/2000 | Bell et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,197,325 B1 | 3/2001 | MacPhee et al. |
| 6,197,934 B1 | 3/2001 | DeVore et al. |
| 6,197,935 B1 | 3/2001 | Doillon et al. |
| 6,210,439 B1 | 4/2001 | Firmin et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,424 B1 | 10/2001 | Vyakarnam et al. |
| 6,312,474 B1 | 11/2001 | Francis et al. |
| 6,328,686 B1 | 12/2001 | Kovac |
| 6,334,872 B1 | 1/2002 | Termin et al. |
| 6,383,201 B1 | 5/2002 | Dong |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | DeVore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,500,464 B2 | 12/2002 | Ceres et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,613,348 B1 | 9/2003 | Jain |
| 6,623,963 B1 | 9/2003 | Muller et al. |
| 6,630,414 B1 | 10/2003 | Matsumoto |
| 6,638,284 B1 | 10/2003 | Rousseau et al. |
| 6,652,594 B2 | 11/2003 | Francis et al. |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,719,795 B1 | 4/2004 | Cornwall et al. |
| 6,723,335 B1 | 4/2004 | Moehlenbruck et al. |
| 6,730,299 B1 | 5/2004 | Tayot et al. |
| 6,736,823 B2 | 5/2004 | Darois et al. |
| 6,743,435 B2 | 6/2004 | DeVore et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B1 | 9/2004 | Abdul Malak et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,893,653 B2 | 5/2005 | Abraham et al. |
| 6,896,904 B2 | 5/2005 | Spiro et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,988,386 B1 | 1/2006 | Okawa et al. |
| 7,025,063 B2 | 4/2006 | Snitkin et al. |
| 7,041,868 B2 | 5/2006 | Greene et al. |
| RE39,172 E | 7/2006 | Bayon et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,594,921 B2 | 9/2009 | Browning |
| 7,615,065 B2 | 11/2009 | Priewe et al. |
| 7,670,380 B2 | 3/2010 | Cauthen, III |
| 7,709,017 B2 | 5/2010 | Tayot |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,799,767 B2 | 9/2010 | Lamberti et al. |
| 7,806,905 B2 | 10/2010 | Ford et al. |

(56) References Cited

U.S. PATENT DOCUMENTS

| | | | |
|---|---|---|---|
| 7,824,420 | B2 | 11/2010 | Eldridge et al. |
| 7,846,171 | B2 * | 12/2010 | Kullas .............. A61F 2/0063 604/15 |
| 7,905,825 | B2 | 3/2011 | Amal et al. |
| 8,142,515 | B2 | 3/2012 | Therin et al. |
| 8,197,837 | B2 | 6/2012 | Jamiolkowski et al. |
| 8,323,675 | B2 | 12/2012 | Greenawalt |
| 8,366,787 | B2 | 2/2013 | Brown et al. |
| 8,418,508 | B2 | 4/2013 | Lecuivre et al. |
| 8,709,094 | B2 | 4/2014 | Stad et al. |
| 8,834,578 | B2 | 9/2014 | Bayon et al. |
| 8,834,864 | B2 | 9/2014 | Odar et al. |
| 8,846,060 | B2 | 9/2014 | Archibald et al. |
| 8,877,233 | B2 | 11/2014 | Obermiller et al. |
| 8,956,373 | B2 | 2/2015 | Ford et al. |
| 8,961,850 | B2 * | 2/2015 | Wood ............. A44B 18/0065 264/285 |
| 9,034,357 | B2 | 5/2015 | Stopek |
| 9,398,943 | B2 * | 7/2016 | Criscuolo ............ A61F 2/0063 |
| 9,445,883 | B2 * | 9/2016 | Lecuivre ............. D04B 21/12 |
| 2002/0095218 | A1 | 7/2002 | Carr et al. |
| 2003/0086975 | A1 | 5/2003 | Ringeisen |
| 2003/0114937 | A1 | 6/2003 | Leatherbury et al. |
| 2003/0133967 | A1 | 7/2003 | Ruszczak et al. |
| 2003/0225355 | A1 | 12/2003 | Butler |
| 2004/0034373 | A1 | 2/2004 | Schuldt-Hempe et al. |
| 2004/0059356 | A1 | 3/2004 | Gingras |
| 2004/0101546 | A1 | 5/2004 | Gorman et al. |
| 2005/0002893 | A1 | 1/2005 | Goldmann |
| 2005/0021058 | A1 | 1/2005 | Negro |
| 2005/0085924 | A1 | 4/2005 | Darois et al. |
| 2005/0113849 | A1 | 5/2005 | Popadiuk et al. |
| 2005/0137512 | A1 | 6/2005 | Campbell et al. |
| 2005/0142161 | A1 | 6/2005 | Freeman et al. |
| 2005/0148963 | A1 | 7/2005 | Brennan |
| 2005/0175659 | A1 | 8/2005 | Macomber et al. |
| 2005/0232979 | A1 | 10/2005 | Shoshan |
| 2005/0267521 | A1 | 12/2005 | Forsberg |
| 2005/0288691 | A1 | 12/2005 | Leiboff |
| 2006/0135921 | A1 | 6/2006 | Wiercinski et al. |
| 2006/0147501 | A1 | 7/2006 | Hillas et al. |
| 2006/0216320 | A1 | 9/2006 | Kitazono et al. |
| 2006/0252981 | A1 | 11/2006 | Matsuda et al. |
| 2007/0299538 | A1 | 12/2007 | Roeber |
| 2009/0192532 | A1 | 7/2009 | Spinnler et al. |
| 2013/0172915 | A1 | 7/2013 | Thomas et al. |

FOREIGN PATENT DOCUMENTS

| | | |
|---|---|---|
| DE | 10019604 A1 | 10/2001 |
| DE | 10043396 C1 | 6/2002 |
| EP | 0194192 A1 | 9/1986 |
| EP | 0248544 A1 | 12/1987 |
| EP | 0276890 A2 | 8/1988 |
| EP | 0372969 A1 | 6/1990 |
| EP | 544485 A1 | 6/1993 |
| EP | 0552576 A1 | 7/1993 |
| EP | 614650 A2 | 9/1994 |
| EP | 0621014 A1 | 10/1994 |
| EP | 0625891 A1 | 11/1994 |
| EP | 0637452 A1 | 2/1995 |
| EP | 0693523 A2 | 1/1996 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 827724 A2 | 3/1998 |
| EP | 0836838 A1 | 4/1998 |
| EP | 0895762 A2 | 2/1999 |
| EP | 898944 A2 | 3/1999 |
| EP | 1017415 A1 | 7/2000 |
| EP | 1052319 A1 | 11/2000 |
| EP | 1055757 A1 | 11/2000 |
| EP | 1216717 A1 | 6/2002 |
| EP | 1216718 A1 | 6/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1782848 A2 | 5/2007 |
| FR | 2244853 A1 | 4/1975 |
| FR | 2257262 A1 | 8/1975 |
| FR | 2308349 A1 | 11/1976 |
| FR | 2453231 A1 | 10/1980 |
| FR | 2715405 A1 | 7/1995 |
| FR | 2724563 A1 | 3/1996 |
| FR | 2744906 A1 | 8/1997 |
| FR | 2766698 A1 | 2/1999 |
| FR | 2771622 A1 | 6/1999 |
| FR | 2779937 A1 | 12/1999 |
| FR | 2859624 A1 | 3/2005 |
| FR | 2863277 A1 | 6/2005 |
| FR | 2884706 A1 | 10/2006 |
| GB | 2051153 A | 1/1981 |
| JP | H0332677 A | 2/1991 |
| JP | H05237128 A | 9/1993 |
| JP | H09137380 A | 5/1997 |
| WO | 8902445 A1 | 3/1989 |
| WO | 8908467 A1 | 9/1989 |
| WO | 9012551 A1 | 11/1990 |
| WO | 9206639 A2 | 4/1992 |
| WO | 9220349 A1 | 11/1992 |
| WO | 9311805 A1 | 6/1993 |
| WO | 9318174 A1 | 9/1993 |
| WO | 9417747 A1 | 8/1994 |
| WO | 9507666 A1 | 3/1995 |
| WO | 9518638 A1 | 7/1995 |
| WO | 9532687 A1 | 12/1995 |
| WO | 9603091 A1 | 2/1996 |
| WO | 9608277 A1 | 3/1996 |
| WO | 9609795 A1 | 4/1996 |
| WO | 9614805 A1 | 5/1996 |
| WO | 9641588 A1 | 12/1996 |
| WO | 9735533 A1 | 10/1997 |
| WO | 9835632 A1 | 8/1998 |
| WO | 9849967 A1 | 11/1998 |
| WO | 9905990 A1 | 2/1999 |
| WO | 9906079 A1 | 2/1999 |
| WO | 9906080 A1 | 2/1999 |
| WO | 9951163 A1 | 10/1999 |
| WO | 0016821 A1 | 3/2000 |
| WO | 0067663 A1 | 11/2000 |
| WO | 0115625 A1 | 3/2001 |
| WO | 0180773 A1 | 11/2001 |
| WO | 2001081667 A1 | 11/2001 |
| WO | 2002/007648 | 1/2002 |
| WO | 02078568 A1 | 10/2002 |
| WO | 03002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A2 | 12/2004 |
| WO | 200511280 A1 | 2/2005 |
| WO | 2005013863 A2 | 2/2005 |
| WO | 2005018698 A1 | 3/2005 |
| WO | 2005105172 A1 | 11/2005 |
| WO | 2006018552 A1 | 2/2006 |
| WO | 2006023444 A2 | 3/2006 |
| WO | 2007048099 A2 | 4/2007 |
| WO | 2009031035 A2 | 3/2009 |
| WO | 2009071998 A2 | 6/2009 |
| WO | 2011027087 A1 | 3/2011 |

OTHER PUBLICATIONS

International Search Report for PCT/EP12/076981 date of completion is Apr. 16, 2013 (2 pages).

Ellouali, M. et al., "Antitumor Activity of Low Molecular Weight Fucans Extracted from Brown Seaweed Ascophyllu nodosum," Anticancer Res., Nov.-Dec. 1993, pp. 2011-2020, 12 (6A).

Malette, W. G. et al., "Chitosan, A New Hemostatic," Ann Th. Surg., Jul. 1983, pp. 55-58, 36.

(56) References Cited

OTHER PUBLICATIONS

Langenbech, M. R. et al., "Comparison of biomaterials in the early postoperative period," Surg Endosc., May 2003, pp. 1105-1109, 17 (7).
Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.
Klinge, U. et al., "Foreign Body Reaction to Meshes Used for the Repair of Abdominal Wall Hernias," Eur J. Surg, Sep. 1999, pp. 665-673, 165.
Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).
Haneji, K et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2),published online Nov. 2009.
Junge, K. et al., "Functional and Morphologic Properties of a Modified Mesh for Inguinal Hernia Repair," World J. Surg., Sep. 2002, pp. 1472-1480, 26.
Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.
Welty, G. et al., "Functional impairment and complaints following incisional hernia repair with different polypropylene meshes," Hernia, Aug. 2001; pp. 142-147, 5.
Varum, K. et al., "In vitro degradation rates of partially N-acetylated chitosans in human serum," Carbohydrate Research, Mar. 1997, pp. 99-101, 299.
Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).
Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220,18(2).
Blondin, C. et al., "Inhibition of Complement Activation by Natural Sulfated Polysaccharides (Fucans) from Brown Seaweed," Molecular Immuol., Mar. 1994, pp. 247-253, 31(4).
Zvyagintseva, T. et al., "Inhibition of complement activation by water-soluble polysaccharides of some far-eastern brown seaweeds," Comparative Biochem and Physiol, Jul. 2000, pp. 209-215, 126(3).
Rosen, M. et al., "Laparoscopic component separation in the single-stage treatment of infected abdominal wall prosthetic removal," Hernia, 2007, pp. 435-440, 11, published online Jul. 2007.
Amid, P., "Lichtenstein tension-free hernioplasty: Its inception, evolution, and principles," Hernia, 2004; pp. 1-7, 8, published online Sep. 2003.
Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).
O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).
Muzzarelli, R. et al., "Reconstruction of parodontal tissue with chitosan," Biomaterials, Nov. 1989, pp. 598-604, 10.
Haroun-Bouhedja, F. et al., "Relationship between sulfate groups and biological activities of fucans," Thrombosis Res., Dec. 2000, pp. 453-459, 100(5).
Blondin, C. et al., "Relationships between chemical characteristics and anticomplementary activity of fucans," Biomaterials, Mar. 1996, pp. 597-603, 17(6).
Strand, S. et al., "Screening of Chitosans and Conditions for Bacterial Flocculation," Biomacromolecules, Mar. 2001, 126-133, 2.
Kanabar, V. et al., "Some structural determinants of the antiproliferative effect of heparin-like molecules on human airway smooth muscle," Br. J. Pharmacol., Oct. 2005, pp. 370-777, 146(3).
Hirano, S. et al., "The blood biocompatibility of chitosan and N-acylchitosans," J. Biomed. Mater. Res., Apr. 1985, 413-417, 19.
Rao, B. et al., "Use of chitosan as a biomaterial: Studies on its safety and hemostatic potential," J. Biomed. Mater. Res., Jan. 1997, pp. 21-28, 34.
Prokop, A. et al., "Water Soluble Polymers for Immunoisolation I: Complex Coacevation and Cytotoxicity," Advances in Polymer Science, Jul. 1998, pp. 1-51, 136.
Collins, R. et al., "Use of collagen film as a dural substitute: Preliminary animal studies," Journal of Biomedical Materials Research, Feb. 1991, pp. 267-276, vol. 25.
Preliminary Search Report from French Patent Office dated Dec. 20, 2006, 3 pages.

\* cited by examiner

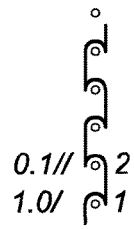 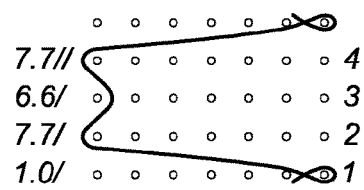 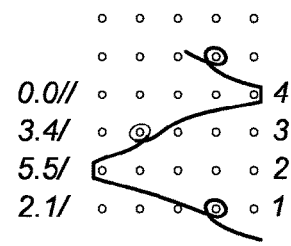
B1      B2      B3
Fig. 1A      Fig. 1B      Fig. 1C
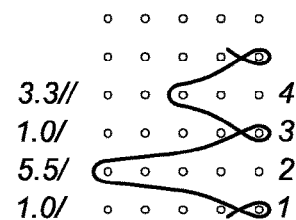
B2
Fig. 2
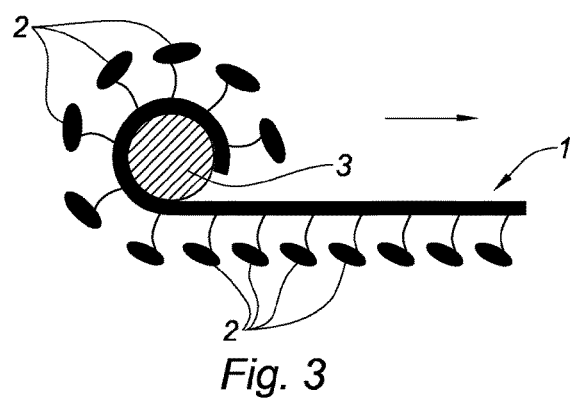
Fig. 3

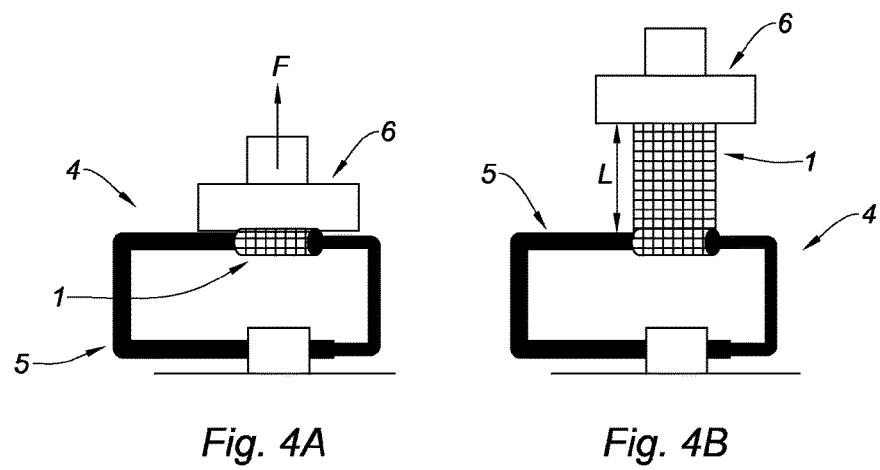
*Fig. 4A*   *Fig. 4B*
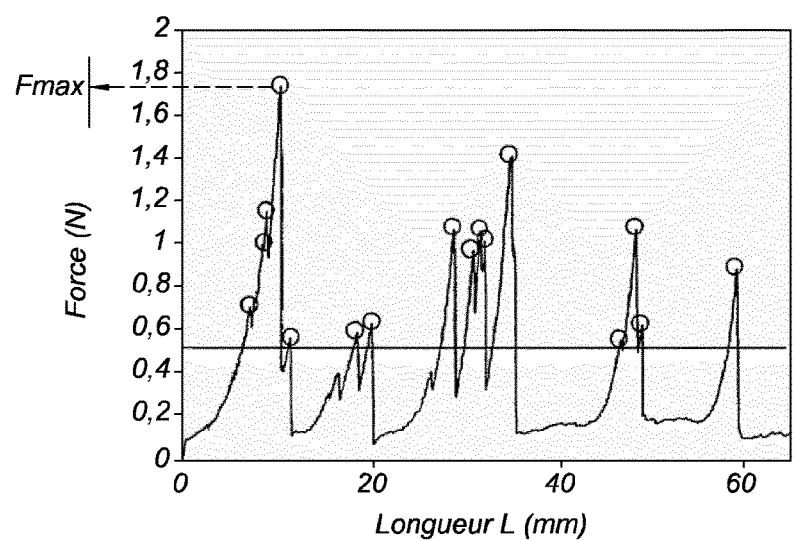
*Fig. 5*

BARBED PROSTHETIC KNIT AND HERNIA REPAIR MESH MADE THEREFROM AS WELL AS PROCESS FOR MAKING SAID PROSTHETIC KNIT

This application is a continuation of U.S. patent application Ser. No. 14/366,393 filed Jun. 18, 2014, which issued as U.S. Pat. No. 9,445,883 on Sep. 20, 2016, which is a National Stage Application of PCT/EP12/076981 filed Dec. 27, 2012, which claims benefit of and priority to French Patent Application Serial No. 11/62535 filed Dec. 29, 2011, and the disclosures of each of the above-identified applications are hereby incorporated by reference in their entirety.

The present invention relates to a prosthetic knit equipped with barbs, capable of being rolled up on itself, then unrolled effortlessly. Such a knit can particularly be used for producing wall-reinforcing prostheses intended to be introduced into a patient by coelioscopy.

Wall-reinforcing prostheses, for example prostheses for reinforcing the abdominal wall, are widely used in the surgical field. These prostheses are intended to treat hernias by temporarily or permanently filling a tissue defect. These prostheses are generally made of biocompatible prosthetic fabric and can have a number of shapes, for example rectangular, circular or oval, depending on the anatomical structure to which they are to be fitted. Some of these prostheses are made from entirely bioresorbable yarns and are intended to disappear after having carried out their reinforcing role while cell colonization takes place and tissue rehabilitation takes over. Other prostheses comprise non-bioresorbable yarns and are intended to remain permanently in the body of the patient.

Some of these prostheses are made from an arrangement of yarns, a knit, a woven fabric or non-woven fabric, comprising barbs that protrude outwards from one face of the prosthesis: these barbs constitute hooks that are able to fix themselves either in another prosthetic fabric, belonging to the same prosthesis or not, or directly in the biological tissues, for example the abdominal wall.

Furthermore, for the sake of minimizing the traumatisms subsequent to any surgical operation, patients are increasingly often operated on via coelioscopic surgery when the type of operation carried out permits it. Coelioscopic surgery requires only very small incisions, through which a trocar is passed, within which the prosthesis is conveyed to the implantation site. Thus open surgery is avoided and the patient can leave hospital rapidly. Coelioscopic surgery is particularly popular in surgical operations carried out in the abdomen, such as for example the treatment of hernias.

However, the trocars used in coelioscopic surgery generally have a relatively small calibrated diameter, which may vary, for example, from 5 to 15 mm, in order to reduce the size of the incision made as much as possible. The prosthesis must therefore be conveyed within a channel of reduced diameter and it must then be deployed at the implantation site.

In order to carry out this step, the prosthesis is generally rolled up on itself in order to make it slide in the channel of the trocar or directly introduced by force. However, when the prosthetic fabric forming the prosthesis comprises barbs on one face, it may happen that these barbs become entangled in the body of the fabric and upset the subsequent deployment of the prosthesis at the implantation site. Furthermore, due to the fact that they are not protected, the barbs may be damaged during the unrolling of the prosthesis or during its transportation through the trocar to the implantation site.

Thus, there remains the need for a prosthetic fabric comprising barbs, that can be used for manufacturing prostheses, such as for example abdominal wall reinforcements, capable of being rolled up on itself in order to be conveyed within a channel such as that of a trocar, without damaging the barbs, and then capable of being completely deployed, and preferably in an easy manner, once it has reached the implantation site in the body of the patient.

The present invention aims to meet such a need.

A first aspect of the invention is a prosthetic knit based on at least a first yarn of biocompatible polymer material defining first and second opposite and openwork faces, and on at least a second biocompatible and heat-fusible monofilament yarn, forming barbs that protrude outwards from at least said first face and are obtained by melting loops generated by said second yarn, the chart followed for the knitting of said first and second yarns on a warp knitting machine having three guide bars B1, B2, B3 being the following, according to the ISO 11676 standard:

Bar B1: 1.0/0.1//
Bar B2: 1.0/7.7/6.6/7.7//
Bar B3: 2.1/5.5/3.4/0.0// said
second yarn following the chart of bar B3.

The knit according to the invention has both openwork faces, which favour cell recolonization, and barbs, suitable for hooking into biological tissues or any other textile, and an ability to be rolled up on itself, then unrolled effortlessly.

The knit according to the invention can be used as is in order to constitute a reinforcing prosthesis for repairing a hernia, or it may constitute one part of a reinforcing prosthesis for repairing hernias: for example, it may be partially or completely coated over part or all of its faces with a coating made of a biocompatible, for example non-stick, material; alternatively or in combination, the knit according to the invention may be combined with another textile in order to form a composite reinforcing prosthesis.

In the present application, the expression "openwork face" is understood to mean that said face comprises openings or pores: these openings or pores are in particular generated by the chart followed for the knitting of the yarns of the knit according to the invention, and may correspond to the various meshes of said knit.

The barbs of the knit according to the invention may protrude from the first face substantially perpendicular to the plane of said face or alternatively along one or more planes that are inclined relative to the plane of said face. These barbs are intended to function as fastening means, either by becoming entangled in one or more arrangements of yarns, fibres, filaments and/or multifilaments of another prosthetic fabric, for example in order to form a composite reinforcing prosthesis, or by anchoring directly in the biological tissues, such as for example an abdominal wall, once the prosthesis comprising this knit or constituted of this knit is implanted. Generally, these barbs have the shape of a shaft, having the diameter of the yarn used for their formation, surmounted by a head having a diameter greater than that of the shaft.

In the knit according to the invention, the chart followed for the knitting of the yarns of the knit generates a particular structure of the knit, that is to say a specific arrangement between the various openings of the faces of the knit, the respective size of these various openings and the position and distribution of the barbs being such that, even if some of the barbs present on the first face are caused to be trapped within some of the openings present on the second face when the knit is rolled up on itself under the effect of an external stress, such as for example the stress exerted by the surgeon when he rolls the knit or the prosthesis comprising the knit up on itself in order to introduce it into a trocar, and subsequently the stress exerted by the internal walls of the trocar, then a large number of the barbs trapped will be released automatically, or under the effect of a very small unrolling force, when said stress is relieved.

The knit according to the invention can be used to produce a reinforcing prosthesis for repairing a hernia. Thus, when the surgeon wishes to implant a prosthesis formed of a knit according to the invention, he can easily roll the knit up on itself, for example by folding the face provided with barbs outwards. It is then possible to introduce the knit according to the invention, thus rolled up, into a trocar, for example having an internal diameter of 10 mm. Once the knit according to the invention has been thus conveyed in the form of a roll to the implantation site via the trocar, it can be unrolled and deployed easily: indeed, even if some of the barbs were trapped within some of the openings present on the second face of the knit during the rolling up of the knit according to the invention and during its passage in the trocar, the particular structure of the knit according to the invention obtained by means of the particular chart followed during the knitting of the knit according to the invention means that these trapped barbs can be released very easily by exerting a minimal force for unrolling the knit. Thus, even if the barbs were entangled when the prosthesis was rolled up, they can be easily disentangled, and the surgeon can deploy the knit and/or the prosthesis easily in order to position it correctly on the implantation site.

The knit can then be fastened either to another fabric, or to a biological wall, owing to the anchoring abilities of the barbs.

In one embodiment of the invention, the first yarn or yarns are monofilament yarns. The first yarn or yarns of the knit according to the invention are those that follow the charts of bars B1 and B2. They constitute the ground structure or alternatively the base of the knit according to the invention, since the second yarn, namely a heat-fusible monofilament yarn, so as to generate the barbs, is regularly cut at the loops that it forms. The generation of barbs from loops made of heat-fusible yarn is known and is described, for example in document WO 01/81667. When the first yarn or yarns are monofilament yarns, the possible presence of protrusions or anchorage points of the barbs is limited and the force needed to unroll the knit after the rolling up as described above is very small.

The first yarns of the knit according to the invention may be made of any biodegradable or non-biodegradable biocompatible material. Thus, the biodegradable materials suitable for the first yarns of the knit of the present invention may be selected from polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), copolymers thereof and mixtures thereof. The non-biodegradable materials suitable for the first yarns of the knit of the present invention may be selected from polyethylene terephthalate (PET), polyamides, aramids, expanded polytetrafluoroethylene, polyurethane, polyvinylidene difluoride (PVDF), butyl ester polymers, polyetheretherketone (PEEK), polyolefins (such as polyethylene or polypropylene), polyethers, copper alloys, silver or platinum alloys, medical grades of steel such as medical-grade stainless steel, and combinations thereof.

In one embodiment of the invention, the first yarns are monofilament yarns made of polyester terephthalate (PET) having a diameter of 0.09 mm. Such yarns have an intrinsic stiffness meaning that when these yarns follow the particular charts of bars B1 and B2 of the knit according to the present invention, the knit obtained naturally tends to return to a flat configuration when it is unrolled under the effect of a stress as described above.

The second heat-fusible monofilament yarn may be made of a bioresorbable or non-bioresorbable material. For example, the heat-fusible monofilament yarn is made of a material selected from polypropylene, polyglycolic acid, polylactic acid, and mixtures thereof. In one embodiment, the heat-fusible monofilament yarn is a polylactic acid monofilament yarn having a diameter of 0.15 mm: such a yarn having such a diameter makes it possible to obtain barbs that have good anchoring abilities in biological tissues or in another openwork textile, while maintaining the ability of the knit according to the invention to be unrolled easily.

Another aspect of the invention is a process for manufacturing a prosthetic knit as described above, comprising the following steps:

i) knitting, on a warp knitting machine, of biocompatible yarns distributed over three guide bars, according to the following chart, according to the ISO 11676 standard:
Bar B1: 1.0/0.1//
Bar B2: 1.0/7.7/6.6/7.7//
Bar B3: 2.1/5.5/3.4/0.0//
the yarn threaded on bar B3 being a heat-fusible monofilament yarn that generates loops that protrude outwards with respect to said first face, ii) cutting, by melting, of each loop, each loop thus generating two barbs.

In the process according to the invention the yarns threaded on bar B1 and bar B2 are the first yarns made of biocompatible polymer material: these yarns may be identical or different. Thus, as seen above, these yarns may be monofilament yarns, in particular monofilament yarns made of polyester terephthalate (PET) having a diameter of 0.09 mm.

In one embodiment of the invention, the yarns are threaded one full, one empty on bars B1 and B2, and one full, three empty on bar B3.

Another aspect of the invention is a knit capable of being obtained according to the above process.

Another aspect of the invention is a prosthesis for repairing a hernia, comprising a knit as described above or obtained according to the process described above.

The knit according to the invention and/or the prosthesis according to the invention may be used in a method for treating a hernia, in particular the abdominal wall. The knit and the prosthesis according to the invention are particularly suitable for coelioscopic or laparoscopic surgery.

The advantages of the present invention are illustrated by means of the experimental section which follows and the following supporting figures:

FIGS. 1A to 1C: are diagrams showing the charts followed for the knitting of the yarns of the knits according to the invention, FIG. 2: is a diagram showing a chart followed for the knitting of the yarns of a knit from the prior art, FIG. 3: is a diagram illustrating the method for rolling up a knit, FIGS. 4A and 4B: are diagrams illustrating the test for evaluating the force for unrolling a rolled-up knit, FIG. 5: shows the curve representing the force applied, in N, as a function of the extension, in mm, of a knit during the unrolling thereof.

EXAMPLE 1

Produced on a warp knitting machine having three guide bars B1, B2 and B3, were a knit A, according to the invention, and a comparative knit B, the chart of which differs from that of the knit according to the invention.

Knit A: according to the invention, having the following chart according to the ISO 11676 standard:
Bar B1: 1.0/0.1//
Bar B2: 1.0/7.7/6.6/7.7//
Bar B3: 2.1/5.5/3.4/0.0//

These charts are illustrated in FIGS. 1A to 1C according to a representation known to a person skilled in the art: the chart of bar B1 is illustrated in FIG. 1A; the chart of bar B2 is illustrated in FIG. 1B and the chart of bar B3 is illustrated in FIG. 1C.

Bar B1 and bar B2 are each threaded 1 full, 1 empty, with a monofilament yarn made of polyester terephthalate (PET) having a diameter of 0.09 mm; bar B3, which gives rise to the barbs, is threaded 1 full, 3 empty, with a heat-fusible monofilament yarn made of polylactic acid having a diameter of 0.15 mm.

Knit B: comparative, having the following chart according to the ISO 11676 standard:
Bar B1: 1.0/0.1//
Bar B2: 1.0/5.5/1.0/3.3//
Bar B3: 2.1/5.5/3.4/0.0//

The chart of bar B2 is illustrated in FIG. 2.

Bar B1 and bar B2 are each threaded 1 full, 1 empty, with a monofilament yarn made of polyester terephthalate (PET) having a diameter of 0.08 mm; bar B3, which gives rise to the barbs, is threaded 1 full, 3 empty, with a heat-fusible monofilament yarn made of polylactic acid having a diameter of 0.15 mm.

For each of the two knits A and B, bar B3 is the one that leads to the formation of the barbs. Since the bars B3 are threaded in an identical manner for the two knits, and these bars have the same chart, the density of the barbs, once the loops have been melted, is the same for both knits.

Once the loops have been melted and the barbs have been formed as described in WO 01/81667, the unrolling properties were evaluated after rolling these knits up on themselves, according to the following test:

for each knit, samples of 5 cm×10 cm were cut,
as shown in FIG. 3, each sample 1 of knit is rolled up on itself around a rod 3 having a diameter of 5 mm, the barbs 2 on the outside, along the direction of the arrow represented in FIG. 3. The roll obtained is then grasped with tweezers and inserted into a trocar having an internal diameter of 10 mm, then pushed until it comes out of the trocar.

On exiting the trocar, as shown in FIG. 4A, the sample 1 in the form of a roll is mounted on a machine 4 equipped with a cell loaded to 25 N, comprising a fixed part 5 and a moving part 6. Around 2 cm of the sample 1 is unrolled and 1 cm of the sample 1 is fastened to the moving part 6. A constant extension rate of 50 mm/min is then applied to the sample 1 tested in order to unroll it, and the corresponding force F needed to maintain said constant extension rate is measured. The force F needed is recorded as a function of the length L of the unrolled portion of the sample 1 until sample 1 is completely unrolled, as shown in FIG. 4B. During the unrolling of the sample 1, the force force F needed may vary as a function of the resistance encountered. In particular, points of resistance, for which the force F for successfully unrolling the sample 1 must be increased, at least occasionally, may appear during the unrolling.

These "points of resistance" are measured as follows: using measured values of the force F and length L of the unrolled portion as indicated above, the curve representing the force F, in newtons, is plotted as a function of the length L of the unrolled portion in mm, of the sample 1. Next, a threshold value is determined for the force F, for example 0.5 N. Each peak of the curve having a value greater than 0.5 N is considered to be a point of resistance. An example of such a curve, showing the peaks counted encircled, is represented in FIG. 5. By virtue of this curve, the maximum force needed, Fmax, is also determined.

The results obtained for knit A according to the invention and comparative knit B are presented in Table I below:

TABLE I

| Sample | Number of tests | Number of "points of resistance" | Average force (N) | Maximum force (N) |
|---|---|---|---|---|
| Knit A | 16 | 52 ± 11 | 1.13 ± 0.33 | 3.54 ± 0.85 |
| Knit B | 20 | 79 ± 8 | 4.01 ± 0.80 | 9.56 ± 1.68 |

As it emerges from this table, the knit according to the invention (Knit A) has significantly fewer points of resistance than the knit from the prior art (Knit B). The average force needed to unroll the knit of the invention, after it has been rolled up on itself then passed through a trocar having an internal diameter of 10 mm is substantially lower than that needed to unroll the knit from the prior art. Likewise, the maximum force needed to unroll knit A according to the invention is practically divided by 3 compared to the maximum force needed in the case of the comparative knit B.

Thus, the knit according to the invention can be unrolled easily after having been rolled up on itself then passed through a trocar having a diameter of 10 mm. The knit can thus be brought to an implantation site during laparoscopic or coelioscopic surgery for repairing a hernia, by means of a trocar, then it can be unrolled without the surgeon having to apply considerable force in order to deploy the knit and/or the prosthesis comprising said knit.

The invention claimed is:

1. A prosthetic knit comprising at least a first monofilament yarn of biocompatible polymer material defining first and second opposite faces, at least the second face including openings, and at least a second biocompatible and heat-fusible monofilament yarn which forms barbs that protrude outward from at least said first face, wherein the openings and the barbs are distributed such that when the knit is rolled upon itself at least some of the barbs present on the first face are caused to be trapped within some of the openings on the second face, and when the knit is unrolled the trapped barbs will be released from the openings of the second face by applying an average force of 1.13±0.33 N.

2. The prosthetic knit according to claim 1, wherein a maximum force of 3.54±0.85 N can be applied to unroll the knit.

3. The prosthetic knit according to claim 1, wherein the openings and the barbs are distributed such that the knit experiences a number of points of resistance of 52±11 when the knit is unrolled at a constant extension rate.

4. The prosthetic knit according to claim 1, wherein the first monofilament yarns are made of polyester terephthalate (PET) having a diameter of 0.09 mm.

5. The prosthetic knit according to claim 4, wherein the second heat-fusible monofilament yarn comprises a material selected from polypropylene, polyglycolic acid, polylactic acid, and mixtures thereof.

6. The prosthetic knit according to claim 4, wherein the second heat-fusible monofilament yarn is a polylactic acid monofilament yarn having a diameter of 0.15 mm.

7. The prosthetic knit according to claim 4, wherein the second heat-fusible monofilament yarn is a polypropylene monofilament yarn having a diameter of 0.15 mm.

8. The prosthetic knit according to claim 1, wherein the barbs are not damaged after unrolling.

9. The prosthetic knit according to claim 1, wherein the first yarn is knit on a warp knitting machine having at least three guide bars B1, B2, B3, according to ISO 11676 standard and the first yarn following the chart of bars B1 and B2:

Bar B1: 1.0/0.1//
Bar B2: 1.0/7.7/6.6/7.7//.

10. The prosthetic knit according to claim 1, wherein the second yarn is knit on a warp knitting machine having at least three guide bars B1, B2, B3, according to ISO 11676 standard and the second yarn following the chart of bar B3:

Bar B3: 2.1/5.5/3.4/0.0//.

11. The prosthetic knit according to claim 1, further comprising a non-stick coating made of a biocompatible material.

12. The prosthetic knit according to claim 1, wherein the first face includes openings.

13. A method for hernia repair comprising
rolling a prosthetic knit up on itself, the knit including at least a first yarn of biocompatible polymer material defining first and second opposite and openwork faces, and at least a second biocompatible and heat-fusible monofilament yarn which forms barbs that protrude outward from at least said first face and are obtained by melting loops generated by the second yarn, said first and second yarns being knit on a warp knitting machine have three guide bars B1, B2, B3, according to ISO 11676 standard and the following chart Bar B1: 1.0/0.1//
Bar B2: 1.0/7.7/6.6/7.7//
Bar B3: 2.1/5.5/3.4/0.0//
the second yarn following the chart of bar B3,
conveying the rolled knit to a site of implantation, and
unrolling the knit by exerting a minimal force to disentangle the barbs the minimal force being an average of 1.13±0.33 N.

14. The method of claim 13, further comprising introducing the rolled knit into a trocar prior to conveying the rolled knit to the site of implantation.

15. The method of claim 13, wherein the first monofilament yarns are made of polyester terephthalate (PET) having a diameter of 0.09 mm.

16. The method of claim 13, wherein the second heat-fusible monofilament yarn comprises a material selected from polypropylene, polyglycolic acid, polylactic acid, and mixtures thereof.

17. The method of claim 16, wherein the second heat-fusible monofilament yarn is a polylactic acid monofilament yarn having a diameter of 0.15 mm.

18. The method of claim 16, wherein the second heat-fusible monofilament yarn is a polypropylene monofilament yarn having a diameter of 0.15 mm.

19. The method of claim 13, wherein the barbs are not damaged after unrolling.

20. The method of claim 14, wherein the yarns comprise an intrinsic stiffness that naturally returns the rolled knit to a flat configuration upon removal from the trocar.

* * * * *